United States Patent

Shinohara et al.

Patent Number: 5,466,847
Date of Patent: Nov. 14, 1995

[54] PROCESS FOR PREPARING HEXAMETHYLCYCLOTRISILAZANE

[75] Inventors: Toshio Shinohara; Akio Yokoo; Muneo Kudo; Motoaki Iwabuchi; Kazuyuki Matsumura, all of Usui, Japan

[73] Assignee: Shin-Etsu Chemical Co., Ltd., Tokyo, Japan

[21] Appl. No.: 330,948

[22] Filed: Oct. 28, 1994

[30] Foreign Application Priority Data

Oct. 29, 1993 [JP] Japan .................................. 5-294194
Feb. 28, 1994 [JP] Japan .................................. 6-054480

[51] Int. Cl.⁶ ........................................................ C07F 7/10
[52] U.S. Cl. ............................................................ 556/409
[58] Field of Search ................................................ 556/409

[56] References Cited

U.S. PATENT DOCUMENTS 4,577,039  3/1986  Arkles et al. ........................ 556/409
4,855,469  8/1989  Baile et al. .......................... 556/409
5,075,474  12/1991 Ohsaki et al. ....................... 556/409
5,084,423  1/1992  Vaahs et al. ...................... 556/409 X
5,245,066  9/1993  Shinohara et al. ................... 556/409

Primary Examiner—Paul F. Shaver
Attorney, Agent, or Firm—Millen, White, Zelano & Branigan

[57] ABSTRACT

A process for preparing hexamethylcyclo-trisilazane by heating octamethylcyclotetra-silazane in the presence of a catalyst such as a Lewis acid or a sulfur compound of the following formula $$(M)_x(R-\underset{\underset{O}{\|}}{\overset{\overset{O}{\|}}{S}}-OH)_y(SO_4)_z \tag{1}$$

wherein M represents Ca, Mg, Al, Fe or $NH_4$, R represents OH, a phenyl group or a substituted phenyl group, x is 0, 1 or 2 and y is 0, 1, 2 or 3 provided that x and y are not zero at the same time, and z is 0, 1, 2 or 3.

10 Claims, No Drawings

PROCESS FOR PREPARING HEXAMETHYLCYCLOTRISILAZANE

BACKGROUND OF THE INVENTION

1. Field of the Invention

This invention relates to a novel process for preparing hexamethylcyclotrisilazane.

2. Description of the Prior Art

As is known in the art, hexamethylcyclo-trisilazane is effective as a liquid phase silification agent for positive resists comprised mainly of novolak resins and is useful as imparting a plasma resistance to the resin (Photochemistry of Silicon, by Hiroyuki Hiraoka, 1990 (No. 1) p.3–19, and Stephan E. Greco, S. Miura, Journal of Electrochem Society, 1991 (No. 3), pp. 810–814).

Known process of preparing hexamethyl-cyclotrisilazane of the following formula (1) include a so-called direct ammonolysis process wherein dimethyldichlorosilane and ammonia gas are reacted with each other (S. D. Brewer and C. P. Haver, J. Am. Chem. Soc., 70 3880 (1948).

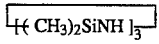
$[-(CH_3)_2SiNH-]_3$     (1)

However, this process has the serious problem that because there is secondarily produced, aside from hexamethylcyclotrisilazane, octamethylcyclotetrasilazane of the following formula (2) in large amounts (about 10 to 30%), the octamethylcyclotetrasilazane side product has to be properly treated on mass-production of hexamethylcyclotrisilazane

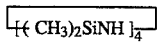
$[-(CH_3)_2SiNH-]_4$     (2)

More particularly, the octamethylcyclo-tetrasilazane has no specific utility, to which little or no attention has been paid for a long while. In recent years, there has been proposed an interesting process that the useful cyclic trimer is prepared from the cyclic tetramer silazane side product through cracking in the presence of a specific type of catalyst in an atmosphere of hydrogen (Japanese Patent Publication No. 63-58838).

However, this process inconveniently makes use of not only hydrogen which has a wide explosion limit and is thus difficult to handle, but also an expensive catalyst such as nickel, platinum or ruthenium. Hence, the processes is not useful for industrially preparing hexa-methylcyclotrisilazane which is a cyclic trimer.

SUMMARY OF THE INVENTION

It is accordingly an object of the present invention to provide a process for efficiently converting octamethylcyclotetrasilazane, which is obtained as a side product when preparing hexamethylcyclotrisilazane by reaction between dimethyldichlorosilane and ammonia, into valuable hexamethylcyclotrisilazane.

As a result of inventive studies on the above preparation, we have found the hexa-methylcyclotrisilazane can be simply obtained in high yield by heating octamethylcyclotetrasilazane in the presence of a catalyst selected from the group consisting of Lewis acids and sulfur compounds Of the following general formula (1)

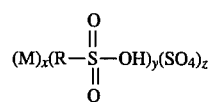

wherein M represents Ca, Mg, Al, Fe or NH$_4$, R represents OH, a phenyl group or a substituted phenyl group, x is 0, 1 or 2 and y is 0, 1, 2 or 3 provided that x and y are not zero at the same time, and z is 0, 1, 2 or 3.

According to the present invention, octamethylcyclotetrasilazane can be efficiently converted into hexamethylcyclotrisilazane by heating the tetrasilazane in the presence of a catalyst selected from an inexpensive Lewis acid and a sulfur compound of the formula (1) without use of any hydrogen gas. This is advantageous from the industrial viewpoint.

DETAILED DESCRIPTION AND EMBODIMENTS OF THE INVENTION

The process for preparing hexamethyl-cyclotrisilazane according to the present invention comprises heating octamethylcyclo-tetrasilazane in the presence of catalyst selected from Lewis acids and sulfur compounds of the afore-indicated formula (1).

The starting octamethylcyclotetrasilazane should effectively be one which is secondarily produced when hexamethylcyclotrisilazane is prepared by reaction between dimethyl dichlorosilane and ammonia. Using such secondarily produced octamethylcyclotetra-silazane, the amount of hexamethylcyclo-trisilazane formed per unit starting material can be maximized. At the same time, some technical problems can be solved including elimination or treatment of octamethylcyclo-tetrasilazane in the form of a solid (melting point of 97° C.) which is left in the distillation column after removal of hexamethylcyclo-trisilazane by distillation.

The Lewis acids used as the catalyst are acids which were defined for acid and base by G. N. Lewis. According to the definition, an acid is an electron- pair acceptor and a base is an electron- pair donor (Modern Chemistry of Iwanami, "Oxidation and Reduction of Acids and Bases" edited by Michinori Ohki and Motoharu Tanaka, p.13–16). The Lewis acids used in the present invention have, respectively, a metal ion and preferably include, for example, aluminum chloride, copper chloride, iron chloride, titanium chloride, aluminum bromide, copper bromide, copper iodide. Of these, it is more preferred to use aluminum chloride, copper chloride, titanium chloride and aluminum bromide although not limitative. These catalysts may be used singly or in combination.

On the other hand, the sulfur compound catalyst is of the following formula (1)

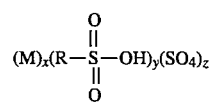

wherein M represents Ca, Mg, Al, Fe or NH$_4$, R represents OH, a phenyl group or a substituted phenyl group, x is 0, 1 or 2 and y is 0, 1, 2 or 3 provided that x and y are not zero at the same time, and z is 0, 1, 2 or 3.

The sulfur compounds of the formula (1) include ammonium sulfate, calcium sulfate, magnesium sulfate, iron sulfates (ferrous and ferric sulfates), aluminum sulfate, benzene-sulfonic acid, p-toluenesulfonic acid, p-toluidine-m- sulfonic acid and the like. Of these, it is preferred to use ammonium sulfate, benzenesulfonic acid, p-toluenesulfonic acid and p-toluidine-m-sulfonic acid. These may be used singly or in combination.

The amount of the catalyst may be properly selected and is generally in the range of 0.1 to 10 wt. %, preferably from 1 to 5 wt. %, based on the amount of octamethylcyclotetrasilazane.

The reaction is favorably effected in an atmosphere of an inert gas such as nitrogen or argon gas and the reaction temperature is in the range of from 70° to 200° C., preferably from 120° to 170° C.

The reaction procedure includes adding a catalyst to starting octamethylcyclotetra-silazane, and heating the mixture, for example, in a distillation column, under reduced or normal pressure to carry out a cracking reaction thereby permitting intended hexamethylcyclo-trisilazane to be distilled off. The cracking time is preferably in the range of from 0.5 to 6 hours, more preferably from 1 to 5 hours. If the cracking time is too short, the reaction does not proceed satisfactorily. On the contrary, when the time is too long, there will be formed a silazane polymer, resulting in a lowering of yield.

The above reaction may be effected in solvents, if necessary. Examples of the solvent include hydrocarbon solvents such as benzene, toluene, n-hexane, cyclohexane and the like, and ether solvents such as n-butyl ether, tetrahydrofuran, dioxane and the like. In this connection, however, any solvents may be used if such solvents are stable in or inert to the reaction system.

As will be apparent from the above, according to the invention, a Lewis acid or sulfur compound catalyst which is readily available and inexpensive, is added to octamethylcyclotetrasilazane, followed by heating and distillation to readily obtain, in high yield, hexamethylcyclotrisilazane which is useful as a silicon reagent in the fields of electronic industries. Thus, the process of the invention is very useful for preparing hexa-methylcyclotrisilazane on the industrial scale.

The present invention is more particularly described by way of examples, which should not be construed as limiting the present invention thereto.

EXAMPLE 1

99.8 g of octamethylcyclotetrasilazane and 3.6 g of aluminum chloride as a catalyst were charged into a 500 ml flask equipped with a thermometer, a nitrogen (inert gas) blowing capillary and a sample discharge port, followed by setting at the top of the flask a distillation column (having glass fine tubes as a filler) having a height of 500 mm and a diameter of 22 mm. When the content was heated to 108° C. in an atmosphere of nitrogen at normal pressure, the octamethylcyclotetrasilazane was melted.

Thereafter, the reaction system was evacuated by means of a vacuum pump. Eight minutes after the evacuation, violent boiling took place. During the course of the cracking distillation over 60 minutes, 92.2 g of hexamethylcyclotrisilazane was obtained as a distillate of a boiling point of 110° C. at 70 mmHg. The yield was 98%.

Examples 2

The general procedure of Example 1 was repeated except that types and amounts of catalysts used were placed by those indicated in Table 1 below, thereby obtaining hexamethylcyclotrisilazane with cracking times and yields being shown in Table 1.

TABLE 1

| Example | Type of catalyst | Amount (g) | Cracking time (minutes) | Yield of hexamethyl-cyclotri-silazane (%) |
|---|---|---|---|---|
| 1 | $AlCl_3$ | 3.6 | 60 | 98 |
| 2 | $TiCl_4$ | 3.8 | 75 | 80 |
| 3 | $FeCl_3$ | 4.0 | 115 | 71 |
| 4 | CuCl | 3.6 | 75 | 71 |
| 5 | CuBr | 3.6 | 95 | 64 |
| 6 | CuI | 4.0 | 90 | 65 |
| 7 | AlBr | 4.0 | 85 | 78 |

EXAMPLE 8

49.9 g of octamethylcyclotetrasilazane and 1.8 g ammonium sulfate as a catalyst were charged into a 200 ml flask equipped with a thermometer, a nitrogen (inert gas) blowing capillary and a sample discharge port, followed by setting at the top of the flask a distillation column (having glass fine tubes as a filler) having a height of 500 mm and a diameter of 22 mm. When the content was heated to 107° C. in an atmosphere of nitrogen at normal pressure, the octamethylcyclotetrasilazane was melted.

Thereafter, the reaction system was evacuated by means of a vacuum pump. Five minutes after the evacuation, violent boiling took place. During the course of the cracking distillation over 60 minutes, 45.6 g of hexamethylcyclotrisilazane was obtained as a distillate of a boiling point of 110° C. at 70 mmHg. The yield was 91%.

EXAMPLES 9–21

The general procedure of Example 8 was repeated except that types and amounts of catalysts used were placed by those indicated in Table 2 below, thereby obtaining hexamethyl-cyclotrisilazane with cracking times and yields being shown in Table 2.

TABLE 2

| Example | Type of catalyst | Amount (g) | Cracking time (minutes) | Yield of hexamethyl-cyclotri-silazane (%) |
|---|---|---|---|---|
| 8 | $(NH_4)_2SO_4$ | 1.8 | 60 | 91 |
| 9 | $CaSO_4$ | 2.0 | 305 | 52 |
| 10 | $MgSO_4$ | 2.0 | 210 | 50 |
| 11 | $Al_2(SO_4)_3$ | 1.8 | 210 | 55 |
| 12 | $Fe_2(SO_4)_3$ | 1.8 | 250 | 54 |
| 13 | | 2.0 | 95 | 75 |
| 14 | | 2.0 | 95 | 78 |
| 15 | | 2.0 | 95 | 80 |
| 16 | $CF_3COOH$ | 1.8 | 300 | 23 |
| 17 | $CH_3COOH$ | 1.8 | 380 | 6 |
| 18 | $H_3PO_4$ | 1.8 | 360 | 17 |
| 19 | $P_2O_5$ | 1.8 | 370 | 7 |
| 20 | $Ph_3P$ | 1.8 | 390 | 5 |
| 21 | $NaH_2PO_4$ | 1.8 | 380 | 5 |

What is claimed is:

1. A process for preparing hexamethylcyclotrisilazane which comprises heating octamethylcyclotetrasilzane in the presence or ammonium sulfate catalyst in an atmosphere of an inert gas.

2. A process according to claim 1, wherein the octamethylcyclotetrasilazane is heated at a temperature ranging from 70° to 200° C.

3. A process according to claim 1, further comprising collecting a distillate of hexamethylcyclotrisilazane under cracking reaction of the octamethylcyclotetrasilazane.

4. A process according to claim 1, wherein said catalyst is present an amount of from 0.1 to 10 wt. % based on the octamethyl-cyclotetrasilazane.

5. A process according to claim 1, wherein the octamethylcyclotetrasilazane is dissolved in a solvent.

6. A process for preparing hexamethylcyclotrisilazane which comprises heating octamethylcyclotetrasilazane in the presence of aluminum chloride catalyst in an atmosphere of an inert gas.

7. A process according to claim 6, wherein the octamethylcyclotetrasilazane is heated to a temperature ranging from 70° to 200° C.

8. A process according to claim 6, further comprising collecting a distillate of hexamethylcyclotrisilazane under cracking reaction of the octamethylcyclotetrasilazane.

9. A process according to claim 6, wherein said catalyst is present in an amount of from 0.1 to 10 wt. % based on the octamethylcyclotetrasilazane.

10. A process according to claim 6, wherein the octamethylcyclotetrasilazane is dissolved in a solvent.

* * * * *